US008193343B2

(12) United States Patent
Strassert et al.

(10) Patent No.: US 8,193,343 B2
(45) Date of Patent: Jun. 5, 2012

(54) MANUFACTURE AND PRODUCTS THEREOF OF PHOTOSENSITIZING NANOMATERIALS AND THEIR USE IN PHOTODYNAMIC TREATMENT

(75) Inventors: Cristian Alejandro Strassert, Münster (DE); Rodrigo Queiroz De Albuquerque, Bayreuth (DE); Yolanda Vida, Münster (DE); Luisa De Cola, Münster (DE)

(73) Assignee: Westfalische Wilhelms-Universitat Munster, Munster (DE)

( * ) Notice: Subject to any disclaimer, the term of this patent is extended or adjusted under 35 U.S.C. 154(b) by 30 days.

(21) Appl. No.: 12/610,935

(22) Filed: Nov. 2, 2009

(65) Prior Publication Data

US 2010/0113554 A1 May 6, 2010

(51) Int. Cl.
*C07B 47/00* (2006.01)
*C07D 487/22* (2006.01)
(52) U.S. Cl. ...................................................... 540/145
(58) Field of Classification Search .................. 540/145
See application file for complete search history.

(56) References Cited

U.S. PATENT DOCUMENTS

| 2005/0058713 | A1 | 3/2005 | Russell et al. |
| 2006/0292112 | A1 | 12/2006 | Röder et al. |
| 2008/0050448 | A1 | 2/2008 | Wilson et al. |

FOREIGN PATENT DOCUMENTS

| DE | 199 36 997 | | 2/2001 |
| DE | 199 36 997 | B4 | 6/2007 |
| JP | 62-104807 | A | 5/1987 |
| JP | 2006-034375 | A | 2/2006 |
| JP | 2007-196104 | A | 8/2007 |
| JP | 2007-231247 | A | 9/2007 |
| WO | WO 01/08704 | A2 | 2/2001 |
| WO | WO 2004/002476 | A2 | 1/2004 |
| WO | WO 2004/089525 | A2 | 10/2004 |
| WO | WO 2004/089525 | A3 | 10/2004 |
| WO | WO 2005/030254 | A2 | 4/2005 |
| WO | WO 2006/106383 | A1 | 10/2006 |
| WO | WO 2008/048190 | A1 | 4/2008 |
| WO | WO 2009/038659 | A2 | 3/2009 |

OTHER PUBLICATIONS

R. Bachor et al., "Photosensitized destruction of human bladder carcinoma cells treated with chlorin $e_6$-conjugated microspheres," Proc. Nat'l. Acad. Sci. USA, vol. 88, pp. 1580-1584, Feb. 1991, (5 pgs).

P. Castan et al., "Polymer-Bound Pyrrole Compounds—V*. on the optical properties of an insoluble polystyrene matrix bearing di- and tetrapyrroles covalently anchored," Reactive Polymers (1991/1992), 1992, pp. 297-310 (14 pgs).
Extended European Patent Office Search Report, EPO Application No. 09 174 795.6 (9 pgs).
M. Hamblin et al., "Photodynamic therapy: a new antimicrobial approach to infectious disease?," Photochemical & Photobiological Sciences, May 2004, 3, pp. 436-450 (15 pgs).
A. Juzeniene et al., "Milestones in the development of photodynamic therapy and fluorescence diagnosis," Photochemical & Photobiological Sciences, Mar. 2007, 6, pp. 1234-1245 (13 pgs).
C.A. Strassert et al., "Comparative photophysical investigation of oxygen and sulfur as covalent linkers on octaalkylamino substituted zinc(II) phthalocyanines," Photochemical & Photobiological Sciences, Apr. 14, 2008, 7, pp. 738-747 (10 pgs).
English translation of abstract of JP 2006-034375 A, Item B4, above (1 pg).
English translation of abstract of JP 2007-196104 A, Item B5, above (1 pg).
English translation of abstract of JP 62-104807 A, Item B6 above (2 pgs).
English translation of abstract of JP 2007-231247 A, Item B7 above (2 pgs).
G. Calzaferri et al., "Host-Guest Antenna Materials;" Angewandte Chemie (Int'l Ed. in English) 2003, 42, pp. 3732-3758 (27 pgs).
Z. Popović et al., "Self-Assembling Living Systems with Functional Nanomaterials," Angewandte Chemie (Int'l Ed. in English) 2007; 46(32), pp. 6188-6191 (5 pgs).
D. Hone et al., "Generation of Cytotoxic Singlet Oxygen Via Phthalocyanine-Stabilised Gold Nanoparticles: A Potential Delivery Vehicle for Photodynamic Therapy," Langmuir, 18, Feb. 12, 2002, pp. 2985-2987 (3 pgs).
K. Ishii et al., "Synthesis and Photophysical Properties of Silica-Gel-Supported Photofunctional (Phthalocyaninato)silicon Complexes," European Journal of Inorganic Chemistry, vol. 2008, issue 19, pp. 2975-2981 (7 pgs).
L. Liz-Marzán et al., "The Assembly of Coated Nanocrystals," Journal of Physical Chemistry, B 2003, 107, pp. 7312-7326 (15 pgs).
A.Z. Ruiz et al., "Synthesis of Zeolite L. Tuning Size and Morphology," Monatshefte für Chemie Chemical Monthly, vol. 136, No. 1, Jan. 2005, pp. 77-89 (15 pgs).
J. Chávez et al., "Core—Shell Nanoparticles: Characterization and Study of Their Use for the Encapsulation of Hydrophobic Fluorescent Dyes," Langmuir 2008, 24, pp. 2064-2071 (8 pgs).
UK Patent Office Search Report, Application No. GB0819978.8 (4 pgs).

*Primary Examiner* — Paul V. Ward
(74) *Attorney, Agent, or Firm* — 24IP Law Group (57) ABSTRACT

A method for the manufacture of a photosensitizing nanomaterial (40) and the products thereof are disclosed. The method for the treatment of a biological target (50) is disclosed. The photosensitizing nanomaterial (40) comprises a metal complex tetrapyrrole derivative (10). The metal complex tetrapyrrole derivative (10) is attached by an axial covalent bond (60) to the surface (25) of a solid nanomaterial (20). The solid nanomaterial (20) has at least one dimension in the nanometer and/or the micrometer range.

10 Claims, 10 Drawing Sheets

MANUFACTURE AND PRODUCTS THEREOF OF PHOTOSENSITIZING NANOMATERIALS AND THEIR USE IN PHOTODYNAMIC TREATMENT

PRIORITY CLAIM AND CROSS-REFERENCE TO RELATED APPLICATIONS

This application claims the benefit of priority under 35 U.S.C. §119 and any other United States or other law of the following: UK (Großbritannien) patent application No. GB 0819978.8 filed on 31 Oct. 2008, which is incorporated herein by reference in its entirety for all purposes.

BACKGROUND

1. Technical Field

The present invention relates to a method for the manufacture of photosensitizing nanomaterials and products thereof and the use of the photosensitizing nanomaterials in photodynamic treatment to inactivate a biological target.

2. Background Art

The manufacture of a photosensitizing metal complex bound to a nanomaterial is known in the art.

Japanese Patent Publication Number JP-A-2007/196104, which is titled "Zeolite material including complex and its utilisation", is assigned to The Nayoga Institute of Japan. The JP-A-2007/196104 disclosure teaches a zeolite solid support including a complex containing a metal of groups 1-13 of the periodic table and an oxygen activation metal complex included in a unit cell of the zeolite solid support and a photosensitizing metal complex retained (preferably included in the unit cell of the zeolite solid support) on the zeolite solid support. The metal contained in the zeolite solid support is for example, at least one of silver, copper, zinc, platinum and palladium. The oxygen activation metal complex is for example, a metal phthalocyanine complex synthesised in the unit cell of the zeolite solid support.

The '104 disclosure does not teach the attachment of a Si(IV) tetrapyrrole metal complex that is covalently bonded directly to the surface of a solid support. The '104 disclosure fails to teach the use of silica nanoparticles as the nanomaterial. There is no disclosure pertaining to the use of the manufactured products for the photodynamic treatment of biological targets.

Japanese Patent Publication Number JP-A-62-104807 is titled "Macromolecular metal complex" and the applicant is Shirai Hiroyashi of Nippon Carbide Kogyo KK, Nittesu KK, Earth Clean KK. The '807 disclosure teaches a metal complex with a high odour-decomposition rate and with outstanding persistency when used as a deodorant. The metal complex is manufactured by bonding a macromolecular compound to a metal phthalocyanine derivative to form an oxidative and reductive metal complex. The macromolecular metal complex can be obtained by bonding to a macromolecular compound (e.g., polystyrene, poly-vinyl alcohol) a metal phthalocyanine derivative containing peripheral substituents, where the central atom M is an oxidative or reductive metal atom (M can be manganese, cobalt, nickel or iron, the substituents can be carbonyl chloride or acetaldehyde). The metal complex is used by dissolution or dispersion in water or an organic liquid, or by adsorption to a zeolite solid support.

The '807 disclosure does not teach the attachment of a Si(IV) tetrapyrrole metal complex covalently bonded directly to the surface of a zeolite L nanomaterial. The '807 disclosure fails to teach the use of silica nanoparticles as the nanomaterial. There is no disclosure in this '807 document pertaining to the use of the manufactured product for the photodynamic treatment for biological targets.

Japanese Patent Publication Number JP-A-2007-231247 is titled "Method for producing phthalocyanine compound pigment micro-particle, phthalocyanine compound pigment micro-particle obtained by the same, ink-jet ink for colour filter, colouring photosensitive resin composition and photosensitive resin transfer material comprising the same and colour filter, liquid crystal display device and CCD device using the same". The applicant of this '247 disclosure is Fuji Film Corp. The '247 disclosure discloses a method for producing a phthalocyanine compound pigment of micro-particles of nanometer size, the micro-particles having excellent dispersion stability and fluidity and achieving high contrast and weather resistance, to provide an inkjet ink for a colour filter, a colouring photosensitive resin composition and a photosensitive resin transfer material comprising the same and to provide the colour filter, a liquid crystal display device and a CCD device (charge coupled device) using the same. The method for producing the phthalocyanine compound pigment micro-particle is achieved as follows. A pigment solution is prepared by dissolving a phthalocyanine compound pigment in a good solvent and mixing with a solvent compatible with the good solvent and providing a poor solvent for the pigment to deposit and produce the pigment and thus prepare a dispersion of the pigment micro-particle of nanometer size. In the process, a high polymer having a mass-average molecular weight $\geqq 1{,}000$ is contained in the dispersion of the pigment micro-particle.

This '247 disclosure teaches pigment micro-particles which consist of phthalocyanine which is not covalently attached to a nanomaterial. The '247 disclosure does not teach the use of the active pigment micro-particles for the photodynamic treatment of biological targets.

One article in the academic journal, Eur. J. Inorg. Chem., 2008, 2975 is titled "Synthesis and photo physical properties of silica-gel supported photo functional (phthalocyaninato) silicon complexes", describes the synthesis and photo physical properties of the silica-gel supported photosensitizing phthalocyaninato silicon complex ($SiPc-SiO_2$). The photo physical properties and surface structures of the silica-gel supported photosensitizing phthalocyaninato) silicon complex ($SiPc-SiO_2$) were investigated in terms of their electronic absorption, fluorescence, singlet ($^1O_2$) oxygen luminescence, and nitrogen adsorption-desorption isotherms. The nitrogen adsorption-desorption isotherms indicate that the planes of SiPcs anchored by axial ligands are parallel to the silica gel surface. In the proposed structure the tetradentate phthalocyaninato (Pc) ligands are considered to coordinate with the silica-gel particles, since the central elements of the SiPcs, such as Si—O—Si—OH, are similar to constituents of the silica-gel. The intensities of fluorescence and singlet oxygen luminescence decrease with an increase in the amount of SiPcs due to interactions between the SiPcs aggregates. By changing the amount of SiPcs, solid materials are prepared based on Pc complexes with both monomeric photo physical properties and a high ability for singlet oxygen generation. The electronic absorption spectrum of the photosensitive (phthalocyaninato) silicon complex ($SiPc-SiO_2$) indicate that a wide optical window is maintained between the Soret and Q absorption bands, even at high concentrations of SiPcs i.e. $[SiPc] \approx 10^{-2}$ M. This results in deep green solids, which is unlike the blue colour of the crystals or concentrated solutions ($>10^{-5}$ M) of $SiPc(OH)_2$.

The Eur. J. Inorg. Chem. disclosure does not teach the attachment of a Si(IV) tetrapyrrole metal complex with a covalent bond to the surface of a zeolite L nanomaterial. The Eur. J. Inorg. Chem. disclosure also fails to teach the use of silica nanoparticles as the nanomaterial. There is no disclosure in the Eur. J. Inorg. Chem. publication pertaining to the use of the photosensitizing phthalocyaninato silicon complex (SiPc-SiO$_2$) in photodynamic therapy.

BACKGROUND OF INVENTION

Photosensitizers are chemical substances that can be used for the photodynamic treatment of a biological target to kill living organisms such as bacteria. Photosensitizers are chemical substances which produce toxic species when exposed to light. Tetrapyrrole metal complexes and metal complex tetrapyrrole derivatives are an example of a photosensitizer. Tetrapyrrole metal complexes have been found to be useful substances for the photodynamic treatment of cancer. An advantage of the tetrapyrrole metal complex as photosensitizers arises due to their low toxicity and high efficiency for the photo-induced inactivation of the biological target. Photosensitizers based on the tetrapyrrole metal complex play an important role in modern technology and have applications in many technical fields. Tetrapyrrole metal complexes and metal complex tetrapyrrole derivatives have been studied as dyes and pigments, but they are also useful chromophores. Tetrapyrrole metal complexes and metal complex tetrapyrrole derivatives have applications in light emitting diodes (LEDs), optical limiting devices, molecular electronics, non-linear optical devices, liquid crystals, gas sensors, chemical catalysts, semiconducting materials, photovoltaic cells, and in electro-chromic displays see for example C. A. Strassert, et al., Photochem. Photobiol. Sci. 7 (2008) 1234].

There is currently a great deal of interest in soluble metal complex tetrapyrrole derivatives. The interest in soluble metal complex tetrapyrrole derivatives is due to their unique electrical, optical and catalytic properties. These properties of the metal complex tetrapyrrole derivatives are negatively affected by a tendency of the metal complex tetrapyrrole derivatives to form aggregates. The aggregation is caused by π-stacking of the conjugated, planar, macrocyclic structure of the aromatic moieties of the metal complex tetrapyrrole derivatives. The tendency towards aggregation leads to a reduction in the solubility of the metal complex tetrapyrrole derivatives and consequently limits their use in a number of applications where a degree of solubility and/or a degree of monomerisation of the metal complex tetrapyrrole derivatives would be favourable. Furthermore, the utilisation of the metal complex tetrapyrrole derivatives for biomedical applications, such as photodynamic treatment requires that the metal complex tetrapyrrole derivatives is effectively dissolved or dispersed in an aqueous medium or in another biocompatible solvent. A further requirement for the use of metal complex tetrapyrrole derivatives in biomedical applications is that the metal complex tetrapyrrole derivative is preferably in a monomeric form, this is because dimers and higher aggregates of the metal complex tetrapyrrole derivatives are inactive in biological applications see for example C. A. Strassert, et al., Photochem. Photobiol. Sci. 7 (2008) 1234.

Photodynamic treatment has been used for the treatment of cancer and other diseases. Photodynamic treatment has received regulatory approval in many countries. Photodynamic treatment of cancer is based on the observation that certain non-toxic photosensitizers accumulate in malignant cancerous cells. One of the best known examples of a non-toxic photosensitizer is a derivative of hematoporphyrin known as Photofrin see for example A. Juzeniene, et al., Photochem. Photobiol. Sci. 6 (2007) 1234 and M Hamblin, et al., Photochem. Photobiol. Sci. 3 (2004) 436.

Photodynamic treatment involves irradiating a photosensitizer with light of an appropriate wavelength to excite the photosensitizer to an excited singlet state. The excited singlet state may then undergo intersystem crossing to a slightly lower energy, but to a longer lived triplet state species. The photosensitizer may then react further via one or both of two possible pathways known as Type I and Type II photo processes. The Type I and the Type II photo processes require the presence of $O_2$. The Type I photo process involves electron transfer reactions from the photosensitizer's triplet state with the participation of a substrate to produce radical ions. The radical ions can then react with the $O_2$ to produce a cytotoxic species, such as a superoxide, and/or a hydroxyl and a lipid radical. The Type II photo process involves energy transfer from the photosensitizer's triplet state to the ground triplet state of molecular oxygen ($^3O_2$), to produce excited state singlet oxygen ($^1O_2$). The $^1O_2$ species has the ability to oxidise a wide variety of biological targets, such as proteins, nucleic acids and lipids. The oxidation of the biological target leads to cytotoxicity within the biological to photo induced inactivate the biological target as a result of the photodynamic treatment; see for example A. Juzeniene, et al., Photochem. Photobiol. Sci. 6 (2007) 1234 and M Hamblin, et al., Photochem. Photobiol. Sci. 3 (2004) 436.

The use of photodynamic treatment has certain advantages over other therapies. One advantage is that photodynamic treatment is dually selective. The photosensitizer can be delivered to a specific site of the biological target, such as a tumour or a pathogen; and the light used in the photodynamic treatment can be accurately pointed to the affected site of the biological target; see for example A. Juzeniene, et al., Photochem. Photobiol. Sci. 6 (2007) 1234 and M Hamblin, et al., Photochem. Photobiol. Sci. 3 (2004) 436.

Although initially developed as a therapy for the treatment of cancer, the most successful application of photodynamic treatment (with FDA approval) has been in the field of ophthalmology for the treatment of age-related macular degeneration. Other photodynamic treatments include, the treatment of psoriasis, arthritis, Barretts' oesophagus and atherosclerosis and restenosis in veins and in arteries target see for example A. Juzeniene, et al., Photochem. Photobiol. Sci. 6 (2007) 1234.

Most of the photosensitizers used for the photodynamic treatment of cancer and other tissue diseases are based on the metal complex tetrapyrrole derivative. Examples of metal complex tetrapyrrole derivative include, porphyrins (HPD), chlorins (BPD, SnEt$_2$, m-THPC), bacteriochlorins (TOOKAD), phthalocyanines (Pc4) and texaphyrins (Lutex). The use of the tetrapyrrole metal complex in photodynamic treatment is due to the low toxicity towards living cells in the absence of photo-irradiation; see for example A. Juzeniene, et al., Photochem. Photobiol. Sci. 6 (2007) 1234 and M Hamblin, et al., Photochem. Photobiol. Sci. 3 (2004) 436.

Chemical substances with a different molecular framework have been used as photosensitizers. These different molecular frameworks include halogenated xanthenes such as Rose Bengal, phenothiazines such as toluidine blue O and methylene blue, and acridines or perylenequinones, such as hypericin see for example M Hamblin, et al., Photochem. Photobiol. Sci. 3 (2004) 436.

The tendency towards aggregation and the lack of solubility and selectivity limit the use of the metal complex tetrapyrrole derivative as a suitable photosensitizer. The uncontrolled diffusion of the metal complex tetrapyrrole derivative to unaffected tissues in the vicinity of the biological target cannot be avoided. Up to now, soluble multifunctional metal complex tetrapyrrole derivatives with selectivity towards biological targets and imaging capabilities have not been described. Such soluble multifunctional metal complex tetrapyrrole derivative would therefore be highly desirable see for example A. Juzeniene, et al., Photochem. Photobiol. Sci. 6 (2007) 1234.

A covalent bond between the metal complex tetrapyrrole derivative and a solid nanomaterial provides a photosensitizing nanomaterial with the ability to prevent the problems associated with aggregation of the metal complex tetrapyrrole derivative.

By manipulating and fine-tuning the size of the solid nanomaterial, the tendency of the metal complex tetrapyrrole derivative, to diffuse into adjacent tissues of the biological target can be reduced. This reduction in the tendency of uncontrolled diffusion of the metal complex tetrapyrrole derivative into adjacent tissues of the biological target increases the selectivity of the photosensitizing nanomaterial when used in the photodynamic treatment of the biological target.

The solid nanomaterial can be zeolite nanocrystals or silica-based nanoparticles and can be nanoparticles that contain silicon, gold, silver, and metal oxides where the metal of the metal oxide can be iron, tin, titanium, aluminium or combinations thereof. The nanoparticles can be a core-shell nanoparticles with free coordinating groups (such as hydroxyl, thiol, amino, carboxylate, phosphate), or any coordinating or chelating group or combinations thereof on the solid nanomaterial surface. These coordinating or chelating groups can be used to form a covalent bond with a variety of molecules. The solid nanomaterial provides a solid support for the attachment of the metal complex tetrapyrrole derivative. In addition, highly luminescent molecules can be entrapped into the cavities and/or defects of the solid nanomaterial, for example into the channels of the zeolite L crystals (see G. Calzaferri, et al., Angew. Chem. Int. Ed. 42 (2003) 3732) or in a matrix of the silica nanoparticles (see J. L. Chavez, et al., Langmuir 24 (2008) 2064). The use the solid nanomaterial provides the possibility for the manufacture of multifunctional arrays of photosensitizing nanomaterials with photosensitizing and imaging properties.

Furthermore functionalisation of the solid nanomaterial surface with targeting groups, e.g. amino, oligopeptide or antibody moieties, can lead to the effective and efficient attachment of the photosensitizing nanomaterial to a specific biological target. This enables more efficient photodynamic treatment of the biological target with the photosensitizing nanomaterial. This functionalisation of the nanomaterial surface increases the selectivity of the photosensitizing nanomaterial when used in the photodynamic treatment of biological targets.

SUMMARY OF THE INVENTION

The present application discloses a method for the manufacture of a photosensitizing material and products thereof. The photosensitizing material is used for the treatment of a biological target. The photosensitizing material has a metal complex tetrapyrrole derivative that is covalently bonded to the surface of a solid material. The present application also discloses the use of the photosensitizing material for the photo induced inactivation of the biological target by using photodynamic treatment.

The metal complex tetrapyrrole derivative is attached to the surface of the solid material by covalent bonds. The surface of the solid material provides an efficient and effective substrate for the manufacture of the photosensitizing material with minor synthetic effort.

The solid material can be zeolite nanocrystals and can be nanoparticles. The nanoparticles can be silicon based nanoparticles and metal oxide nanoparticles. The solid material has at least one dimension in the nanometer and/or the micrometer range.

The metal complex tetrapyrrole derivative may be a Si(IV) phthalocyanine metal complex and derivates thereof.

The biological target can be a virus, a eukaryotic or a prokaryotic cell such as the bacterium E. Coli.

The solid material avoids problems associated with aggregation of metal complex tetrapyrrole derivative.

In general, any application where the monomeric form of the metal complex tetrapyrrole derivative is required can be implemented by the present disclosure.

Photo physical and photo biological investigations of the manufactured photosensitizing material described by the present application provide results which show the monomeric binding of the metal complex tetrapyrrole derivative to the solid material.

The photosensitizing material possesses the ability to produce singlet oxygen molecules. The photosensitizing material has been used for the photodynamic treatment of the biological target E. Coli. The photosensitizing material has been used for the photodynamic treatment of the biological target Neisseria Gonorrhoeae.

In an aspect of the present disclosure, a liquid such as water can be decontaminated by photodynamic treatment by using the photosensitizing material provided by the present disclosure.

Very little toxicity in the absence of irradiation (i.e., dark toxicity) when using the photosensitizing material for the photodynamic treatment of the biological target is achieved since the solid material and the metal complex tetrapyrrole derivative of the photosensitizing material are biocompatible. Therefore the photosensitizing materials can be used for in vitro and/or in vivo photodynamic treatment of infections, cancers or other diseases in any conceivable pharmaceutical formulation.

In a further aspect of the present disclosure, the methodology is extended to materials with luminescent dopants entrapped into matrices, defects, cavities or channels of the solid material. The channels of zeolite L crystals of the can be loaded with a highly luminescent molecule such as DXP. The luminescent materials give rise to the photosensitizing material having both imaging and photosensitizing properties.

In a further aspect of the present disclosure, the surface of the photosensitizing material can be functionalised with functional groups. The functional groups provide a means for the photosensitizing material to have an enhanced affinity to be attracted to a specific biological target. This enhanced affinity increases the selectivity of the photosensitizing material for the biological target. The functionalisation of the surface of the photosensitizing material with amino groups can increase the dispersion ability of the photosensitizing material in an aqueous medium and can also facilitate the attachment of the photosensitizing material to a cell surface, thus increasing the selectivity of the photosensitizing material, as well as the effectiveness for the photo inactivation of the biological target.

The multifunctional properties of the photosensitizing materials are desirable for the simultaneous photodynamic treatment of the biological target and for the labelling of cells and viruses. Furthermore, the photodynamic treatment with the photosensitizing material provides a targeted and selective treatment means, thus avoiding the uncontrolled diffusion of the metal complex tetrapyrrole derivative into the environment and/or neighbouring tissue.

DESCRIPTION OF FIGURES

FIG. 8 shows the results of experiments using the photosensitizing nanomaterial in the photodynamic treatment of the biological target E. Coli.
a) Utilisation of the photosensitizing nanomaterials with zeolite L as the solid nanomaterial and Si(IV) phthalocyanine chloride as the metal complex tetrapyrrole derivative, according to an aspect of the present disclosure. Percentage of dead biological target with progressing irradiation time is shown; white bars represent the data for zeolite L crystals, black bars represent data for photosensitizing nanomaterials without irradiation, striped bars represent data for irradiated photosensitizing nanomaterials.
b) Utilisation of the photosensitizing nanomaterials with silica nanoparticles as the solid nanomaterial and Si(IV) phthalocyanine chloride as the metal complex tetrapyrrole derivative, according to an aspect of the present disclosure. Percentage of dead biological target with progressing irradiation time is shown; white bars represent the data for silica nanoparticles, black bars represent data for the photosensitizing nanomaterials without illumination, striped bars represent data for irradiated photosensitizing nanomaterials.
c) As in a), the differences being the 80 times smaller size of the zeolite L crystals used as the solid nanomaterial, tetra-t-butyl-substituted Si(IV) phthalocyanine hydroxide used as the metal complex tetrapyrrole derivative, and an amino coating of the photosensitizing nanomaterial. The gray columns represent non-functionalised zeolite L crystals without irradiation.

DETAILED DESCRIPTION

For a complete understanding of the present disclosure and the advantages thereof, reference is made to the following detailed description taken in conjunction with the accompanying figures.

It should be appreciated that the various aspects of the present disclosure discussed herein are merely illustrative of the specific ways to make and use the technology and do not limit the scope of technology when taken into consideration with the claims and the following detailed description and the accompanying figures. It should be observed that features from one aspect of the disclosure can be combined with features from other aspects of the disclosure.

The teachings of the cited documents should be incorporated by reference into the description.

Photodynamic treatment provides a means for the treatment of a biological target 50 by the photo-induced inactivation of the biological target 50 (such as prokaryotic and eukaryotic cells and viruses) and for the treatment of cancer and other diseases. A source of light excites a photosensitizing nanomaterial 40 which in turn generates highly reactive singlet oxygen ($^1O_2$) from non-reactive triplet oxygen molecules ($^3O_2$), see for example A. Juzeniene, et al., Photochem. Photobiol. Sci. 6 (2007) 1234 and M Hamblin, et al., Photochem. Photobiol. Sci. 3 (2004) 436.

Since the highly reactive singlet oxygen ($^1O_2$) also damages neighbouring unaffected (healthy) tissue near the biological target 50, an optical fibre is usually used for treatments involving in vivo photodynamic treatment. The optical fibre is used to ensure that irradiation of the biological target 50 of the affected tissue occurs and to prevent irradiation of the unaffected tissue near the biological target 50. The metal complex tetrapyrrole derivative 10 (when not bound to a stationary nanomaterial) diffuses through the entire body of a patient under photodynamic treatment. Therefore many weeks after this photodynamic treatment, a patient is required to avoid exposure to intense sources of photo irradiation (i.e. light and sun), see for example A. Juzeniene, et al., Photochem. Photobiol. Sci. 6 (2007) 1234 and M Hamblin, et al., Photochem. Photobiol. Sci. 3 (2004) 436.

The highly efficient production of the singlet oxygen $^1O_2$ can be achieved by the use of the metal complex tetrapyrrole derivative 10. The metal complex tetrapyrrole derivative 10 can convert up to 70% of absorbed light (red photons) into the singlet oxygen $^1O_2$, see for example C. A. Strassert, et al., Photochem. Photobiol. Sci. 7 (2008) 1234.

The functionalisation of the metal complex tetrapyrrole derivative 10 with appropriate axial or peripheral substituents can further shift the absorption/emission of the metal complex tetrapyrrole derivative 10 to the desired near infrared region (700 nm-900 nm). The near infrared region (700 nm-900 nm) is the optimal therapeutic region for photodynamic treatment involving in vivo applications. Examples of the axial or peripheral substituents include, but are not limited to, amino, hydroxyl, chloro, alkyl, alkoxy, sulfanyl, siloxy or aryl groups, see for example C. A. Strassert, et al., Photochem. Photobiol. Sci. 7 (2008) 1234.

The present application teaches a method for the manufacture and products thereof of a photosensitizing nanomaterial 40. The present application also teaches the use of the photosensitizing nanomaterial 40 for the photodynamic treatment of the biological target 50. The metal complex tetrapyrrole derivative 10 is attached to the solid nanomaterial 20 by the covalent bond 60. The covalent bond 60 is made between the nanomaterial surface 25 of the solid nanomaterial 20 and the metal of the metal complex tetrapyrrole derivative 10.

The making of a covalent bond 60 between the metal complex tetrapyrrole derivative 10 and a solid nanomaterial 20 overcomes at least some of the problems associated with diffusion of the metal complex tetrapyrrole derivative 10 into the neighbouring tissue of a biological target 50. This happens because by means of a covalent bond 60 between a stationary solid nanomaterial 20 and the metal core, the metal complex tetrapyrrole derivative 10 is not free to diffuse away from the biological target 50, i.e., to diffuse through the body of the patient under photodynamic treatment. The covalent bond 60 is very stable and is an irreversible bond between the metal complex tetrapyrrole derivative 10 and a nanomaterial surface 25 of the solid nanomaterial 20.

The presence of the covalent bond 60 within the photosensitizing nanomaterial 40 overcomes at least some of the problems associated with aggregation and diffusion of the metal complex tetrapyrrole derivative 10 as the metal complex tetrapyrrole derivative 10 is bound monomerically to the nanomaterial surface 25.

The axial covalent bond 60 ensures that the metal complex tetrapyrrole derivative 10 is attached onto the nanomaterial surface 25 of the solid nanomaterial 20.

The metal complex tetrapyrrole derivative 10 can be one of a Si(IV) phthalocyanine complex or a derivative thereof, with any peripheral substituent, such as tert-butyl groups.

The metal complex tetrapyrrole derivative 10 can be a metal complex of a porphyrin, a benzo porphyrin, a phthalocyanine, a napthalocyanine or any derivatives thereof.

The metal complex tetrapyrrole derivative 10 can have axial reactive groups, such as chloride or hydroxide. The axial groups of the metal complex tetrapyrrole derivative 10 react with the anchoring groups present on the nanomaterial surface 25, during the reaction the covalent bond 60 is formed between the metal of the metal complex tetrapyrrole derivative 10 and the nanomaterial surface 25.

Figure 9:
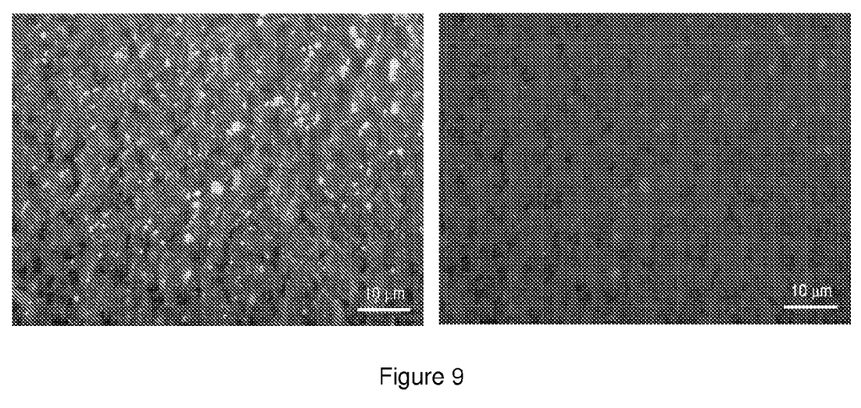
FIG. 9 shows two fluorescence images of the photosensitizing nanomaterial with zeolite L crystals as the solid nanomaterial (in this case doped with the green emitting dye DXP and the surface modified with amino groups), and tetra-t-butyl-substituted Si(IV) phthalocyanine hydroxide as the metal complex tetrapyrrole derivative. On the left side, the green luminescence upon selective excitation of DXP is shown. On the right side, the red luminescence upon selective excitation of the tetra-t-butyl-substituted Si(IV) phthalocyanine hydroxide is shown.
Figure 10:
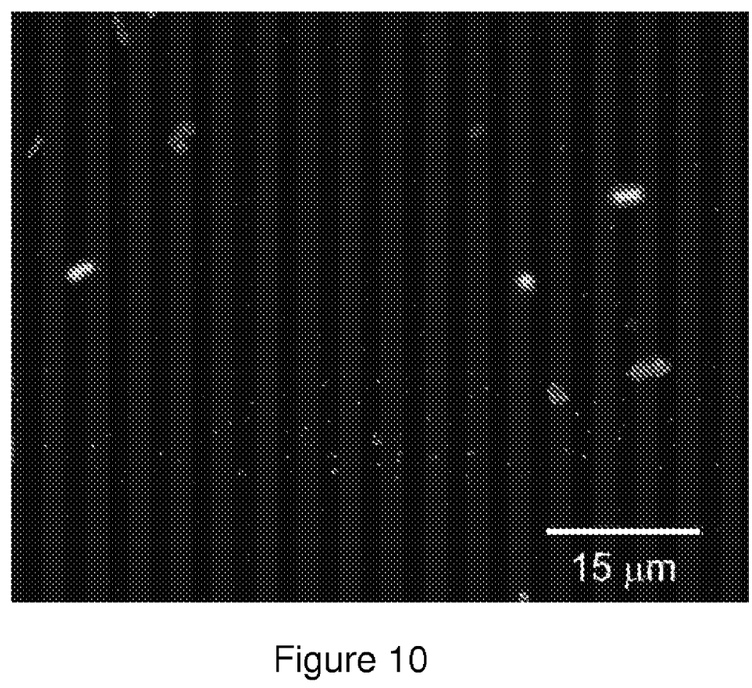
FIG. 10 shows a confocal fluorescence image of E. Coli cells labelled with the photosensitizing nanomaterial with zeolite L crystals as the solid nanomaterial (in this example doped with the green emitting dye DXP and surface modified with amino groups), and tetra-t-butyl-substituted Si(IV) phthalocyanine hydroxide as the metal complex tetrapyrrole derivative. This shows that doping with fluorescent dyes and surface modification with amino groups provides a labelling tool for the biological target, to which the photosensitizing nanomaterial will show a greater affinity.

In a further aspect of the present disclosure, the metal complex tetrapyrrole derivative 10 can include derivatives of the metal complex tetrapyrrole derivative 10, with for example, peripheral tert-butyl groups (FIGS. 9, 10), axial chloride (FIGS. 1, 2, 3, 4, 5) or hydroxide groups (FIGS. 9, 10).

The solid nanomaterials 20 can include, but is not limited to, zeolite nanocrystals and/or a silicon-based nanoparticle. The nanoparticles can also comprise silicon, gold, silver, and metal oxides where the metal of the metal oxide can be iron, tin, titanium, aluminium or combinations thereof. The nanoparticles can include core-shell nanoparticles which have for example a core of iron or gold and a silica shell. The nanoparticles can also have ferromagnetic properties. The solid nanomaterial can have coordinating groups (such as hydroxyl, thiol, amino, carboxylate, phosphate), or any coordinating or chelating group or combinations thereof on the solid nanomaterial surface 25. These coordinating or chelating groups can be used to form a covalent bond with a variety of molecules. The solid nanomaterial 20 can be a zeolite L crystal or silica nanoparticles. The solid nanomaterial 20 can also be a mixture of solid nanomaterials 20.

The solid nanomaterial 20 is non-toxic to the biological target 50. This non-toxicity of the solid nanomaterial 20 makes it useful for the in vivo photodynamic treatment of the biological target 50.

The solid nanomaterial 20 and the metal complex tetrapyrrole derivative 10 are non toxic to biological targets 50. The covalent bond 60 between the solid nanomaterial 20 and the metal complex tetrapyrrole derivative 10 overcomes problems associated with diffusion of the metal complex tetrapyrrole derivative 10 to nearby (healthy) biological tissue of the biological target 50.

Figure 1:
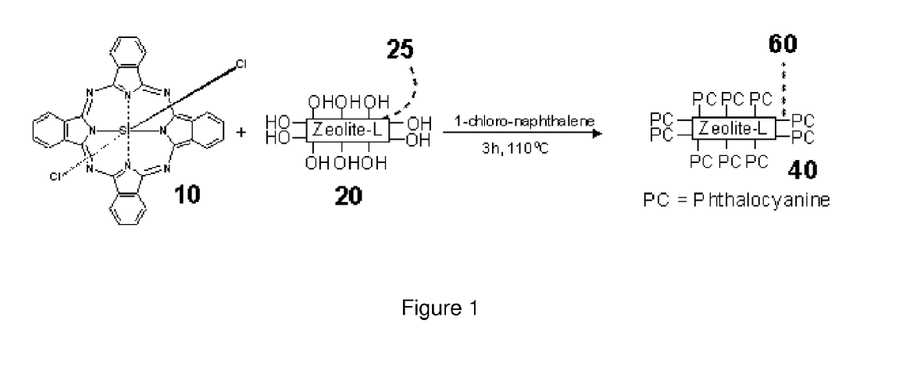
FIG. 1 shows a schematic for the manufacture of a photosensitizing nanomaterial in an example of the present disclosure.

FIG. 1 illustrates an example of the method for the manufacture of the photosensitizing nanomaterial 40. In this example the metal complex tetrapyrrole derivative 10 is a Si(IV) phthalocyanine chloride complex. The solid nanomaterial 20 is provided by zeolite L crystals. The nanomaterial surface 25 is the surface of the solid nanomaterial 20. As noted above, the solid nanomaterial 20 can be, but is not limited to, zeolite L crystals or silica nanoparticles, or a mixture of both.

Figure 2:
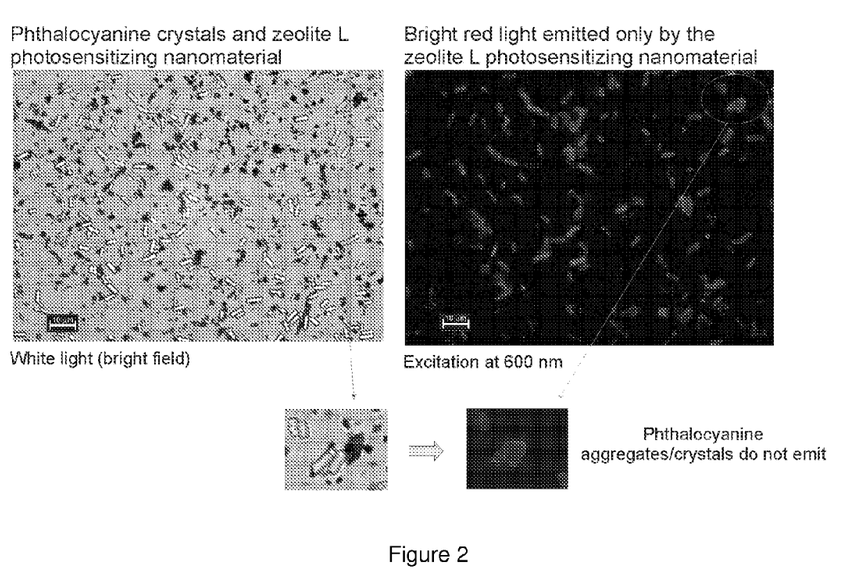
FIG. 2 shows an image of aggregated crystals of metal complex tetrapyrrole derivative (in this case Si(IV) phthalocyanine chloride) which are unable to emit red light (left), in contrast with the highly emissive monomeric metal complex tetrapyrrole derivative bound to the surface of a solid nanomaterial (in this case zeolite L) (right). The emission observed is attributed to the monomeric form of the metal complex tetrapyrrole derivative on the zeolite L surface.

FIG. 2 shows the transmission and fluorescent microscope images of a suspension of the photosensitizing nanomaterial 40. In this example of the present disclosure, the photosensitizing nanomaterials 40 consists of silicon (IV) phthalocyanine chloride as the metal complex tetrapyrrole derivative 10 bound to a zeolite L crystal as the solid nanomaterial 20. In this example it is shown that the crystals of the silicon (IV) phthalocyanine chloride complex are aggregates. These aggregates do not exhibit emission. When the silicon (IV) phthalocyanine chloride complex is covalently attached to the nanomaterial surface 25 of the zeolite L crystals as a monomer, the metal complex tetrapyrrole derivative 10 shows a strong luminescence.

Figure 3:
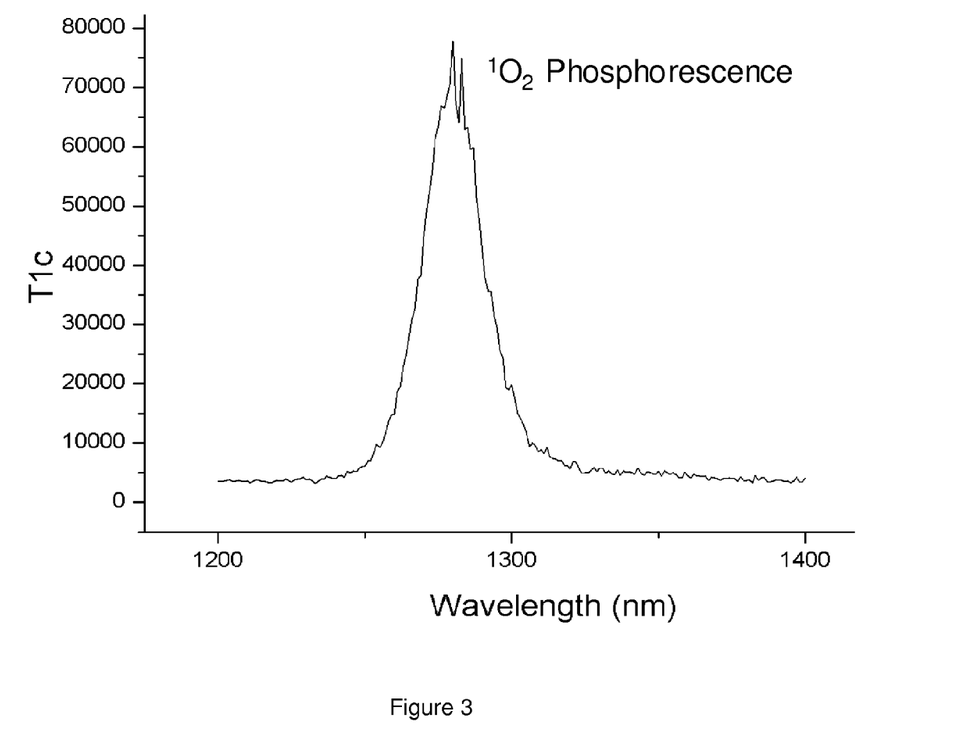
FIG. 3 shows the characteristic phosphorescence of singlet oxygen molecules, which can only be produced in the presence of the monomeric form of the metal complex tetrapyrrole derivative (in this example Si(IV) phthalocyanine chloride) bound to the surface of the solid nanomaterial (in this case zeolite L) according to an example of the present disclosure. The spectrum was recorded from a suspension of the photosensitizing nanomaterial in $CD_2Cl_2$ at room temperature, $\lambda_{exc}=670$ nm.

We refer now to FIG. 3, which shows the characteristic phosphorescence of singlet oxygen $^1O_2$. The singlet oxygen $^1O_2$ is produced by reaction of triplet oxygen ($^3O_2$) with the monomeric form of the silicon (IV) phthalocyanine chloride complex, which is present on the surface of the zeolite L crystals, according to an example of the present disclosure. The generation of the singlet oxygen $^1O_2$ was investigated by measuring the near IR emission spectrum of the photosensitizing nanomaterials 40 in a suspension with deuteriated dichloromethane as the solvent ($CD_2Cl_2$). FIG. 3 shows the characteristic phosphorescence spectrum from the singlet oxygen $^1O_2$ produced by the silicon (IV) phthalocyanine chloride bound to the nanomaterial surface 25 of the zeolite L crystal. The results demonstrate the ability of the photosensitizing nanomaterial 40 to photo-produce singlet oxygen ($^1O_2$). Furthermore, the characteristic emission of the singlet oxygen ($^1O_2$) can be quenched with a singlet oxygen quencher, such as DABCO (diazabicyclooctane), which reinforces that the manufactured photosensitizing nanomaterial 40 is able to generate singlet oxygen. The investigation of a solution of the pure metal complex tetrapyrrole derivative 10 (in this aspect silicon (IV) phthalocyanine chloride) in the same solvent ($CD_2Cl_2$), but not bound to a nanomaterial surface 25 of the solid nanomaterial 20, does not show any generation of the singlet oxygen ($^1O_2$). No characteristic phosphorescence can be detected.

Figure 4:
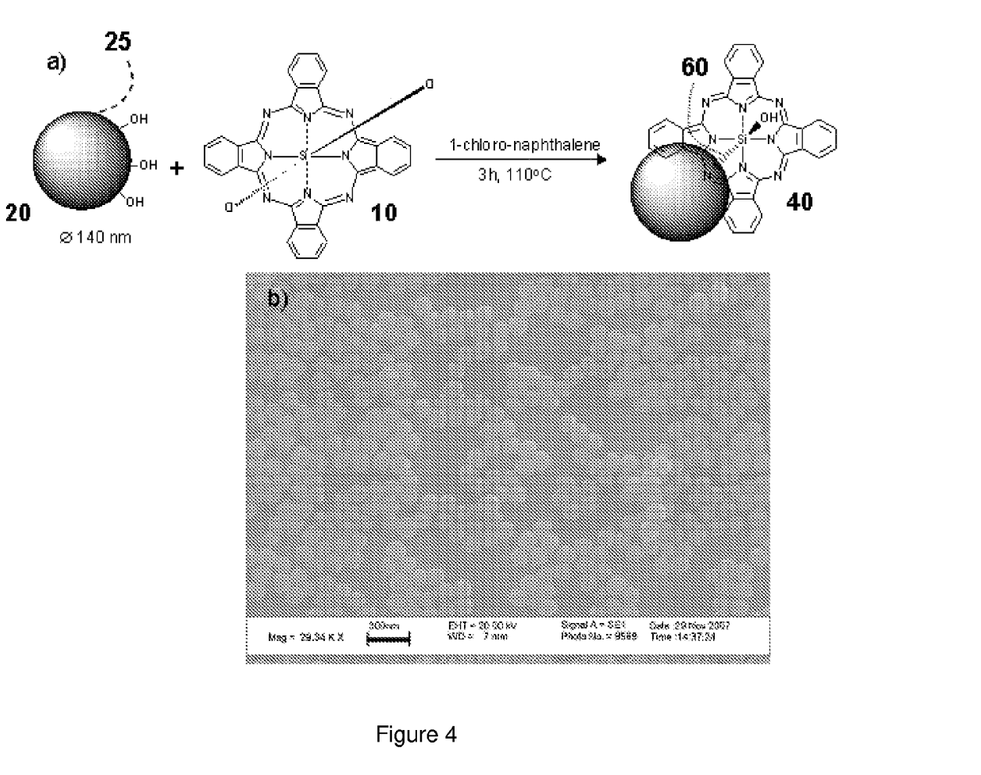
FIG. 4 shows a) schematic for the manufacture of the photosensitizing nanomaterial with silica nanoparticles as the solid nanomaterial and Si(IV) phthalocyanine chloride as the metal complex tetrapyrrole derivative. b) A SEM image of the obtained photosensitizing nanomaterial with silica nanoparticle as the solid nanomaterial and Si(IV) phthalocyanine chloride as the, according to an example of the present disclosure.

FIG. 4a shows another aspect of the present disclosure for the manufacture of the photosensitizing nanomaterials 40. In this aspect of the disclosure, the solid nanomaterial 20 is silica nanoparticles and the metal complex tetrapyrrole derivative 10 is provided by a Si(IV) phthalocyanine chloride complex.

In FIG. 4a, the photosensitizing nanomaterial 40 has a Si—O—Si (siloxane) axial covalent bond 60. The siloxane axial covalent bond 60 is formed between the metal (silicon atom) of the metal complex tetrapyrrole derivative 10, and an oxygen atom of a terminal hydroxyl group present on the nanomaterial surface 25 and silicon atoms present on the nanomaterial surface 25 of the solid nanomaterial 20.

FIG. 4b shows the SEM images of the photosensitizing nanomaterials 40 comprising of the metal complex tetrapyrrole derivative 10 (in this example, silicon (IV) phthalocyanine chloride) bound to the nanomaterial surface 25 of the of the solid nanomaterial 20 (in this example, silica nanoparticles). FIG. 4b demonstrates that the structure of the solid nanomaterial 20 remains unaffected after the attachment of the metal complex tetrapyrrole derivative 10. This reflects the stability of the photosensitizing nanomaterials 40.

Figure 5:
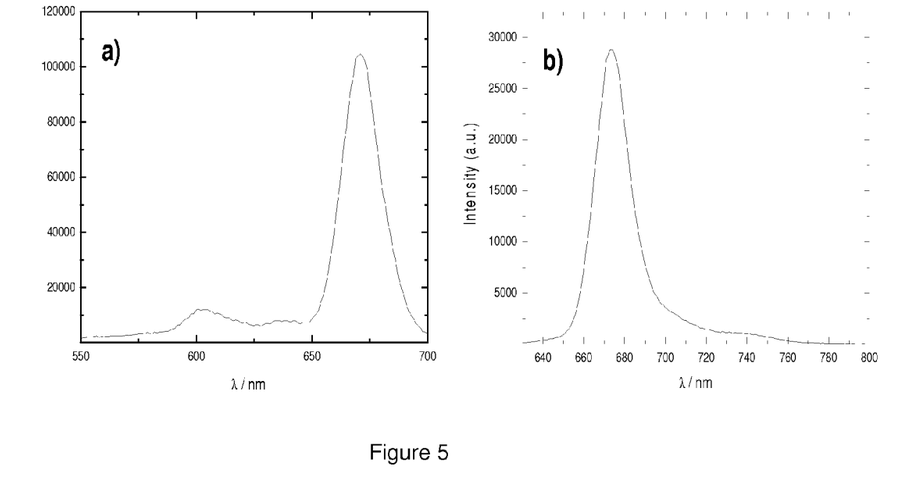
FIG. 5 shows the a) excitation ($\lambda_{em}=674$ nm) and b) emission ($\lambda_{ex}=610$ nm) spectra of the photosensitizing nanomaterial, with silica nanoparticle as the solid nanomaterial and Si(IV) phthalocyanine chloride as the metal complex tetrapyrrole derivative, according to an aspect of the present disclosure, in $CD_2Cl_2$ at room temperature. The emission observed is attributed to the monomeric form of the metal complex tetrapyrrole derivative on the nanoparticle surface.

FIG. 5 shows a) excitation ($\lambda_{em}$=674 nm) and b) emission ($\lambda_{ex}$=610 nm) spectra of the photosensitizing nanomaterials 40 of the metal complex tetrapyrrole derivative 10 (in this example, silicon (IV) phthalocyanine chloride) bound to the nanomaterial surface 25 of the solid nanomaterial 20 (in this example, silica nanoparticles), in $CD_2Cl_2$ suspension at room temperature. Such an emission spectra can only be attributed to the monomeric form of the metal complex tetrapyrrole derivative 10 (in this example, silicon (IV) phthalocyanine chloride), which is covalently attached to the nanomaterial surface 25 of the solid nanomaterial 20 as a monomer.

Figure 6:
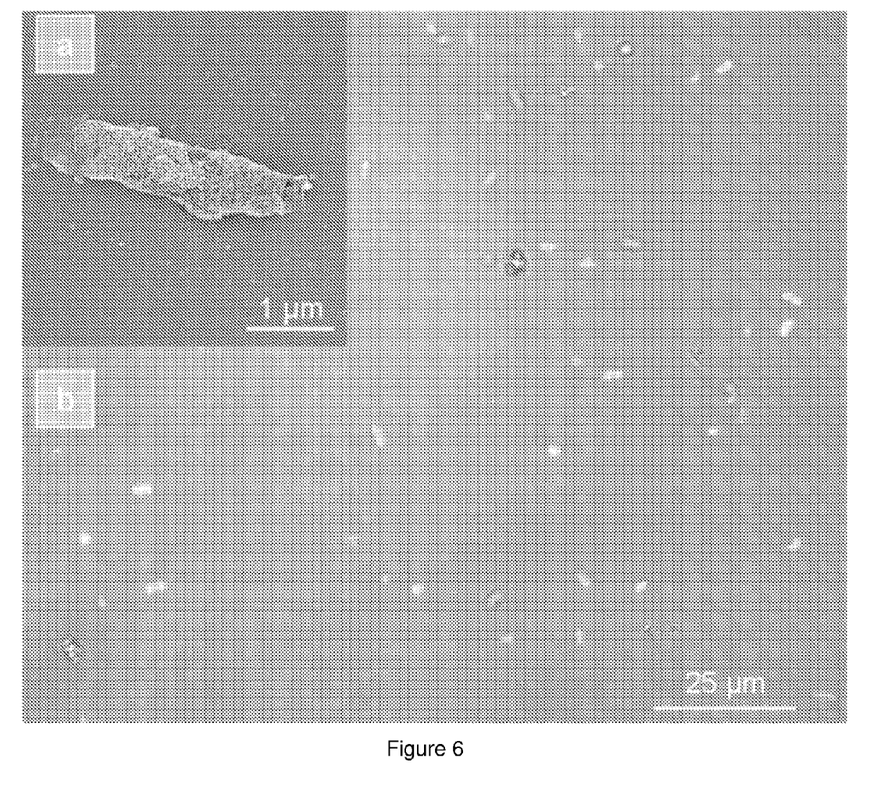
FIG. 6a shows an overlay of confocal fluorescence and bright field microscopy images of labeled E. coli bacteria. The rod-like shaped cells are labeled by a green emitting photosensitizing nanomaterial ($\lambda_{exc}=488$ nm).
FIG. 6b shows a scanning electron microscopy image of an E. coli cell covered with the photosensitizing nanomaterial.

FIG. 6a shows an overlay of confocal fluorescence and bright field microscopy images of labeled *E. coli* bacteria. The rod-like shaped cells are labeled by a green emitting photosensitizing nanomaterial ($\lambda_{exc}$=488 nm). FIG. 6b shows a scanning electron microscopy image of an *E. coli* cell covered with the photosensitizing nanomaterial.

Figure 7:
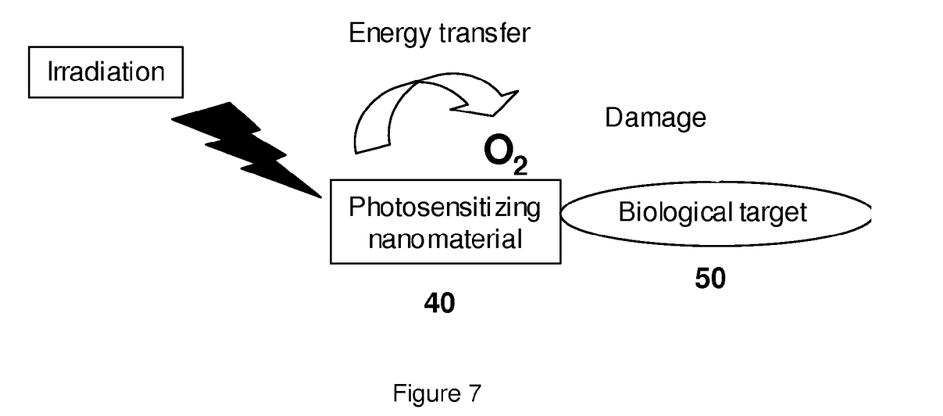
FIG. 7 shows a schematic of the photodynamic treatment process, which induces photo inactivation of biological targets by irradiating the photosensitizing nanomaterial with light.

A further aspect of the present disclosure is shown in FIG. 7. FIG. 7 shows a scheme of the photodynamic treatment process used to photo inactivate the biological target 50 by irradiation of the photosensitizing nanomaterials 40 with light. In this aspect the photosensitizing nanomaterial 40 is irradiated with light to generate the singlet oxygen $^1O_2$ by energy transfer from the metal complex tetrapyrrole derivative 10 to the triplet oxygen $^3O_2$. The singlet oxygen $^1O_2$ has the ability to damage the biological target 50. Examples of the implementation of the photosensitizing nanomaterials 40 for the photodynamic treatment of a biological target 50 include, but are not limited to, the photodynamic decontamination of water. In an example of the present disclosure the photosensitizing nanomaterial 40 has been used for the treatment of the biological target 50 *E. Coli*. The biological target 50 can also be for example *Neisseria Gonorrhoeae* or even a bacterial cell that is resistant to treatment by an antibiotic.

Figure 8:
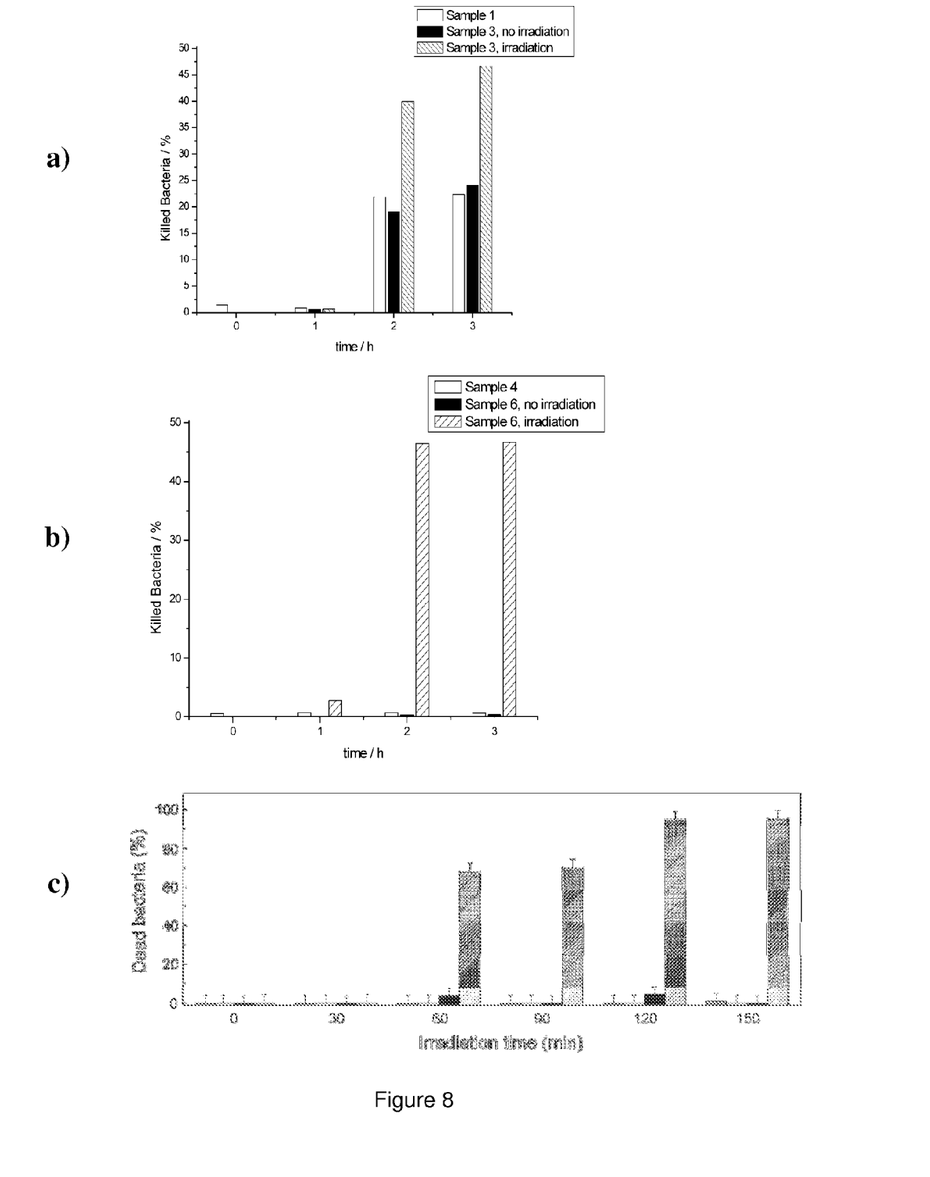

FIG. 8 shows the results of experiments using the photosensitizing nanomaterial 40 for the photodynamic treatment of the biological target 50 *E. Coli*. In these examples of the present disclosure, the biological target 50 *E. Coli* is present as a suspension in water. a) Utilization of photosensitizing nanomaterials 40 with zeolite L crystals as the solid nanomaterial 20 and Si(IV) phthalocyanine chloride as the metal complex tetrapyrrole derivative 10, according to an aspect of the present disclosure. A percentage of dead biological targets with progressing irradiation time is shown; white bars represent the data for zeolite L crystals, black bars represent data for photosensitizing nanomaterials 40 without illumination, striped bars represent data for irradiated photosensitizing nanomaterials 40. b) Utilisation of photosensitizing nanomaterials 40 with silica nanoparticles as the solid nanomaterial 20 and Si(IV) phthalocyanine chloride as the metal complex tetrapyrrole derivative 10, according to an aspect of the present disclosure. The percentage of dead biological targets with progressing irradiation time is shown; white bars represent the data for the solid nanoparticles 10, black bars represent data for the photosensitizing nanomaterials 40 without illumination, striped bars represent data for irradiated photosensitizing nanomaterials 40. c) The same as in a), the difference being the 80 times smaller size of the zeolite L crystals used as the solid nanomaterial 20, the tetra-t-butyl-substituted Si(IV) phthalocyanine hydroxide used as the metal complex tetrapyrrole derivative 10, and the amino coating of the photosensitizing nanomaterial 40. The grey columns represent non-functionalised zeolite L crystals without illumination. These results demonstrate the photodynamic effect, exemplifying that the irradiation of the photosensitizing nanomaterials with light results in significant cell-death of the biological target 50. It is observed that by decreasing the size of the zeolite L crystals and the surface modification with amino groups, increases the efficiency of the photodynamic treatment used to photo inactivate the biological target 50 of *E. Coli*.

It was surprising that the photosensitizing nanomaterial 40 also exhibits biocompatibility and a lack of toxicity to the biological target 50. The concurrent irradiation and functionalisation of the solid nanomaterial 20 with the metal complex tetrapyrrole derivative 10 causes significant inactivation of the biological target 50.

FIG. 9 shows two fluorescence images of the photosensitizing nanomaterial with zeolite L nanocrystals as the solid nanomaterial 20 (in this case doped with the green emitting dye DXP and the nanomaterial surface 25 modified with amino groups), and tetra-t-butyl-substituted Si(IV) phthalocyanine hydroxide as the metal complex tetrapyrrole derivative 10. On the left, the green luminescence upon selective excitation of DXP is shown. On the right, the red luminescence upon selective excitation of the Si(IV) phthalocyanine is shown. These results demonstrate the effective functionalisation of the solid nanomaterial 20 with both DXP and the monomeric metal complex tetrapyrrole derivative 10.

FIG. 10 shows a confocal fluorescence image of the biological target 50—*E. Coli* cells which have been labelled with the photosensitizing nanomaterial 40. The photosensitizing nanomaterial 40 is in this example consists of zeolite L crystals as the solid nanomaterial 20 (in this case doped with the green emitting dye DXP and the nanomaterial surface 25 modified with amino groups), and tetra-t-butyl-substituted Si(IV)

phthalocyanine hydroxide as the metal complex tetrapyrrole derivative 10. FIG. 10 demonstrates that doping the photosensitizing nanomaterial 40 with fluorescent dyes and surface amino modification provides an effective labelling tool for the biological target 50. The amino functionalisation enhances the adherence of the photosensitizing nanomaterial 40 to the biological target 50, which increases the labelling capability of the photosensitizing nanomaterial 40.

The manufacture of the photosensitizing nanomaterial 40 is conducted in the dark and under an inert atmosphere as follows: a suspension of the solid nanomaterial 20 is saturated with the metal complex tetrapyrrole derivative 10 in an anhydrous aromatic solvent such as toluene or 1-chloro-naphthalene. The suspension is then continuously stirred and continuously heated for a period of between 3 to 24 hours. During the heating and stirring of the suspension the photosensitizing nanomaterial 40 is manufactured in the suspension. Once the photosensitizing nanomaterial 40 is manufactured, it is filtered from the suspension and washed by pouring fresh amounts of the same anhydrous aromatic solvent that was used in the manufacture step over the manufactured photosensitizing nanomaterial 40. The photosensitizing nanomaterial 40 is then dried prior to use.

In an aspect of the present disclosure the inert atmosphere is provided by an inert gas such as nitrogen or argon. In a further aspect of the present disclosure the anhydrous organic solvent used for the manufacture is the same anhydrous organic solvent used to wash the manufactured photosensitizing nanomaterial 40.

EXAMPLES

Zeolite L crystals—50 nm long Zeolite L crystals were purchased from Clariant.

4 µm long zeolite L crystals were manufactured according to the procedure described by A. Z. Ruiz, et al., Monatsh. Chem. 136 (2005) 77.

Silica nanoparticles. The silica nanoparticles were manufactured by following the procedure described by L. M. Liz-Marzan, et al., J. Phys. Chem. B 107 (2003) 7312.

Example 1

Manufacture of Solid Nanomaterial 20 Loaded with DXP Dye

The zeolite L crystals were exchanged with potassium ions prior to being loaded with the DXP dye. The DXP dye (N,N'-Bis(2,6-dimethylphenyl)perylene-3,4,9,10-tetracarboxylic diimide) was purchased from Aldrich and used without further purification. The DXP dye was inserted into the 50 nm long zeolite L crystals from the gas phase by following the procedure described by G. Calzaferri, et al., Angew. Chem. Int. Ed. 42 (2003) 3732.

Example 2

Manufacture of Photosensitizing Nanomaterial 40

1 mg of the metal complex tetrapyrrole derivative 10, 5 mg anhydrous tetra-tert-butyl Si(IV) phthalocyanine dihydroxide, purchased from Sigma-Aldrich and used as provided, was added to a toluene suspension containing the DXP-loaded zeolite L solid nanomaterial 20 (as described in example 1) and sonicated for 45 minutes. The resultant mixture was sonicated for 10 minutes and then heated at 110° C. for 3 hours.

The manufactured photosensitizing nanomaterial 40 was washed with anhydrous toluene, until no metal complex tetrapyrrole derivative 10, anhydrous tetra-tert-butyl Si(IV) phthalocyanine dihydroxide, could be detected in the supernatant liquid.

In an alternative aspect the resultant mixture comprising the manufactured photosensitizing nanomaterial 40 was centrifuged to separate the manufactured photosensitizing nanomaterial 40. The manufactured photosensitizing nanomaterial 40 was washed by suspending the manufactured photosensitizing nanomaterial 40 in anhydrous toluene, water/Genapol (from Clariant and used as received) and water until no anhydrous tetra-tert-butyl Si(IV) phthalocyanine dihydroxide, could be detected in the supernatant liquid.

Example 3

Functionalisation of Photosensitizing Nanomaterial 40 with Amino Groups

The photosensitizing nanomaterial 40 (as described in Example 2) comprising the DXP dye and the metal complex tetrapyrrole derivative 10, anhydrous tetra-tert-butyl Si(IV) phthalocyanine dihydroxide was functionalised on the surface of the photosensitizing nanomaterial 40 with amino groups by following the procedure described by Z. Popovic, et al. Angew. Chem. Int. Ed. 46 (2007) 6188.

The crystals of the photosensitizing nanomaterial 40 were dried at 60° C. and stored in the dark.

Example 4

Manufacture of Photosensitizing Nanomaterial 40

1 mg of dry metal complex tetrapyrrole derivative 10 Si(IV) phthalocyanine dichloride, purchased from Sigma-Aldrich and used as provided, was added to a suspension of 1-chloro-naphthalene containing the solid nanomaterial 20, 4 µm long zeolite L crystals. The resultant mixture was sonicated for 10 minutes and then heated at 110° C. for 3 hours. The manufactured photosensitizing nanomaterial 40 was washed with anhydrous 1-chloronaphthalene, until no metal complex tetrapyrrole derivative 10 Si(IV) phthalocyanine dichloride, could be detected in the supernatant liquid.

The crystals of the photosensitizing nanomaterial 40 were dried at 60° C. and stored in the dark.

Example 5

Manufacture of Photosensitizing Nanomaterial 40

1 mg of dry metal complex tetrapyrrole derivative 10 Si(IV) phthalocyanine dichloride purchased from Sigma-Aldrich and used as provided, was added to a suspension of 1-chloro-naphthalene containing the solid nanomaterial 20, silica nanoparticles. The resultant mixture was sonicated for 10 minutes and then heated at 110° C. for 3 hours. The manufactured photosensitizing nanomaterial 40 was washed with anhydrous 1-chloro-naphthalene, until no metal complex tetrapyrrole derivative 10 Si(IV) phthalocyanine dichloride could be detected in the supernatant liquid.

The crystals of the photosensitizing nanomaterial 40 were dried at 60° C. and stored in the dark.

Example 6

Biological Target 50—*E. Coli*

The bacteria samples of the biological target 50, of *E. Coli* strain BL21 (DE3) pLys were taken from an incubated stock solution in Lysogeny broth (LB) medium and were re-suspended in a phosphate buffered saline (PBS, pH 7.4) solution. The concentration of bacteria in solution was estimated by optical density.

Example 7

Biological Target 50—*Neisseria Gonorrhoeae*

The bacteria samples of the biological target 50, of *Neisseria Gonorrhoeae* strain N400 (recA inducible) was maintained on agar containing NaCl (5 g L$^{-1}$, Roth), K$_2$HPO$_4$ (4 g L$^{-1}$, Roth), KH$_2$PO$_4$ (1 g L$^{-1}$, Roth), Proteose Peptone No. 3 (15 g L$^{-1}$, BD), Starch (0.5 g L$^{-1}$, Sigma Aldrich), IsoVitaleX Enrichment (10 mL L$^{-1}$, BD) and were grown overnight at 37° C. and 5% CO$_2$. The *Neisseria Gonorrhoeae* N400 cells were re-suspended in supplemented medium with PBS (pH 7.4), L-glutamine (2 mM, Invitrogen), sodium pyruvate (8 mM, Invitrogen), HEPES (30 mM, Roth) and D-glucose (11 mM, Roth). The concentration of bacteria cells in solution was estimated by optical density.

Example 8

*E. Coli* Labelled by Photosensitizing Nanomaterial 40

1 mg of the photosensitizing nanomaterial 40 loaded with DXP dye (as described in example 3) was suspended in 1 mL PBS (1x, pH=7.4), and sonicated for 1 hour. The solution of *E. Coli* in PBS (1x, pH 7.4), with a concentration of approximately 10$^8$ cell mL$^{-1}$, and the suspension containing the photosensitizing nanomaterial 40, were mixed in equal volumes in a cuvette. The mixture was then placed in a cuvette-holder equipped with a magnetic stirrer. After 30 minutes an aliquot of the suspension was taken and analysed in the fluorescence microscope in order to see the *E. Coli* bacteria labelled with the green fluorescence provided by the DXP dye.

Example 9

Photodynamic Treatment of *E. Coli*

1 mg of photosensitizing nanomaterial 40 (any of the ones previously described in example 3, example 4 and example 5) was suspended in 1 mL PBS (1x, pH=7.4), and sonicated for 1 hour. The solution of *E. Coli* in PBS (pH 7.4), with a concentration of approximately 10$^8$ cell mL$^{-1}$, and the suspension containing the photosensitizing nanomaterial 40, were mixed in equal volumes in a cuvette. The mixture was then placed in a cuvette-holder equipped with a magnetic stirrer and irradiated using a tungsten lamp (irradiance at the cuvette of 3 mW cm$^{-2}$). An aperture and a cut-off filter ($\lambda$>570 nm) were used together with a water filter, in order to cut-off the blue and the infrared part of the irradiation beam, respectively. Every 30 minutes aliquots of 6.2 μL were taken and propidium iodide was added to reach a final concentration of 48 μM. The samples were allowed to stain in the dark for 15 minutes before analysis on the fluorescence microscope, where pictures were recorded under bright field illumination and under excitation at 500-600 nm. For each picture the total number of bacteria was counted with the aid of a counting chamber, and compared to the number of PI-stained bacteria. Control experiments without illumination and without phthalocyanine functionalisation were performed using analogous methodology as described.

Example 10

Photodynamic Treatment of *Neisseria Gonorrhoeae*

1 mg of photosensitizing nanomaterial 40 was suspended in 500 μL PBS (pH=7.4) supplemented with L-glutamine, sodium pyruvate, HEPES and D-glucose and sonicated for between 30 and 60 minutes. A solution of *Neisseria Gonorrhoeae*, with a concentration of approximately 10$^8$ cell mL$^{-1}$, and the suspension containing the photosensitizing nanomaterial 40, were mixed in equal volumes in a cuvette. The mixture was then placed in a cuvette-holder equipped with a magnetic stirrer and irradiated using a tungsten lamp (irradiance at the cuvette of 3 mW cm$^{-2}$). An aperture and a cut-off filter ($\lambda$>570 nm) were used together with a water filter, in order to cut-off the infrared part of the irradiation beam, respectively. Every 30 minutes aliquots were taken and propidium iodide was added to reach a final concentration of 48 μM. The samples were allowed to stain in the dark for 15 minutes before analysis on the fluorescence microscope, where pictures were recorded under bright field illumination and under excitation at 500-600 nm. For each picture the total number of bacteria was counted with the aid of a counting chamber, and compared to the number of PI-stained bacteria. Control experiments without illumination and without phthalocyanine functionalisation were performed using analogous methodology as described.

Fluorescence emission and excitation spectra of the photosensitizing nanomaterial 40 suspended in CH$_2$Cl$_2$ were recorded by using a HORIBA Jobin-Yvon IBH FL-322 Fluorolog 3 spectrometer. The phosphorescence spectrum of $^1$O$_2$ in CD$_2$Cl$_2$ was recorded by using a HORIBA Jobin-Yvon IBH FL-322 Fluorolog 3 spectrometer equipped with an air-cooled Hamamatsu H9170-75 (InP/InGaAs) PMT detector.

Fluorescence microscopy was carried out with an Olympus IX-71 equipped with a Hg high pressure lamp, air objective 100×1.0, an Olympus U-MNB2 excitation cube and a colour camera. The confocal microscopy images have been recorded utilizing a Leica TCS SPE microscope, equipped with a 488 nm diode laser using a scan rate of 400 MHz.

The scanning electron microscopy images have been recorded using a Zeiss 1540 EsB Dual Beam Focused Ion Beam/Field Emission Scanning Electron Microscope (SEM) with a working distance of 8 mm and an electronic high tension (EHT) of 3 kV.

Having thus described the present technology in detail, it is to be understood that the foregoing detailed description of the technology is not intended to limit the scope of the technology thereof. What is desired to be protected by letters patent is set forth in the following claims.

List of Reference Numerals

10 Metal complex tetrapyrrole derivative
20 Solid nanomaterial
25 Nanomaterial surface
30 Reaction conditions
40 Photosensitizing nanomaterial
50 Biological target
60 Covalent bond

The invention claimed is:

1. A method for the manufacture of a photosensitizing nanomaterial the method comprising:
  adding a solid material to an anhydrous aromatic solvent to form a suspension,
  saturating the suspension with a compound comprising metal complex tetrapyrrole,
  heating and stirring the suspension under an inert atmosphere in the dark, filtering and washing the manufactured photosensitizing nanomaterial from the suspension; and drying the photosensitizing nanomaterial.

2. The method according to claim 1, wherein the compound comprising the metal complex tetrapyrrole is selected from a group consisting of the metal complex tetrapyrrole comprising one of a porphyrin, a benzo porphyrin, a phthalocyanine, a napthalocyanine or any derivatives thereof.

3. The method according to claim 1, wherein the solid material is selected from the group consisting of zeolite L crystals, silica-based nanoparticles or metal oxides.

4. The method according to claim 1, wherein the solid material has ferromagnetic properties.

5. The method according to claim 1, wherein the heating is at a temperature of between 90° C. and 220° C.

6. The method according to claim 1, wherein the aromatic organic solvent is selected from the group comprising of toluene or 1-chloro-naphthalene.

7. The method according to claim 1, wherein the heating is for between 2 hours and 24 hours.

8. The method according to claim 1, wherein the mixture is at least one of heated and agitated.

9. The method according to claim 1, wherein the solid material is loaded with a DXP dye.

10. The method according to claim 1, wherein the photosensitizing nanomaterial is functionalised with amino groups.

* * * * *